United States Patent [19]

Markofsky et al.

[11] Patent Number: 4,952,700

[45] Date of Patent: Aug. 28, 1990

[54] PREPARATION OF ISOXAZOLINES AND ISOXAZOLES

[75] Inventors: Sheldon B. Markofsky, Olney; Steven A. Kothe, Baltimore, both of Md.

[73] Assignee: W.R. Grace & Co.-Conn., New York, N.Y.

[21] Appl. No.: 185,657

[22] Filed: Apr. 25, 1988

[51] Int. Cl.$^5$ .................. C07D 261/04; C07D 261/08; C07D 261/12; C07D 261/14

[52] U.S. Cl. ..................................... 548/240; 548/243; 548/244; 548/245; 548/246; 548/247; 548/248

[58] Field of Search ............... 548/240, 243, 244, 245, 548/247, 248, 246

[56] References Cited

U.S. PATENT DOCUMENTS

| | | | |
|---|---|---|---|
| 3,513,180 | 5/1970 | Fenton | 260/398 |
| 3,945,998 | 3/1976 | Anderson et al. | 546/275 |
| 4,092,326 | 5/1978 | Shipchandler | 548/237 |
| 4,479,888 | 10/1984 | Koch et al. | 548/335 |
| 4,761,460 | 8/1988 | Otsuka et al. | 548/521 |

OTHER PUBLICATIONS

Rahman et al., Chemical Abstracts, vol. 101, No. 54969v (1984).
Harada et al., *Chem. Pharm. Bull.*, vol. 28, pp. 3296–3303 (1980).
Kornblum et al., J.A.C.S. 80, 4333, (1958).

*Primary Examiner*—Mukund J. Shah
*Assistant Examiner*—E. Bernhardt
*Attorney, Agent, or Firm*—Howard J. Troffkin

[57] ABSTRACT

A process for forming isoxazolines or isoxazoles by contacting, in the presence of base, a nitro compound, a cyclic anhydride and a dipolarophile. The dicarboxylic acid is readily regenerated to be again reused as the dehydrating agent of additional nitro compound.

26 Claims, No Drawings

PREPARATION OF ISOXAZOLINES AND ISOXAZOLES

BACKGROUND OF THE INVENTION

The present invention is directed to an improved process for forming isoxazolines and isoxazoles from nitroparaffins. The resultant products are useful in the formation of 1,3 amino alcohols and 1,3 ketoalcohols from the isoxazolines and 1,3-diketones and 1,3 ketoamines from the isoxazoles which are required in providing pharmaceutical agents. The resultant products are also known to be useful water treatment agents.

The reaction of nitroalkanes with phenyl isocyanate in the presence of a catalytic amount of triethylamine and with acetic anhydride in the presence of a base have been extensively studied. In the reaction of a primary nitroalkane with phenyl isocyanate as the dehydrating agent, one produces a nitrile oxide which dimerizes to produce a furoxan when run neat or, when in the presence of an olefin, an isoxazoline [T. Mukaiyama et al. J.A.C.S. 82, 5339 (1960); R. Husiegen Angew. Chem. 75 604 (1963)]. The utilization of an isocyanate presented several problems which included the cost and toxicity of the isocyanate as well as the ready deactivation of the isocyanate as a dehydrating agent by other materials in the reaction zone.

In the reaction of the primary nitroalkane with acetic anhydride, initial studies reported evidence which refuted a mechanism encompassing the formation of nitrile oxide intermediate. However, A. Rahman et al. Pak. J. Sci. Res. 30, 91–4 (1978) showed that when the reaction is conducted in the presence of a non-polar solvent and a dipolarophile, one does obtain isoxazoline. Acetic anhydride has been the reagent of choice by those skilled in this area because it is a readily available, inexpensive and is a liquid under ambient reaction conditions. Acetic anhydride can thus be easily dispensed into the reaction medium and has good solubility in common solvents. A final reason for viewing acetic anhydride as the desired dehydrating agent is its simple structure which is viewed as a means of inhibiting side reactions and possibly by-product formation. More recently, Rahman et al., in J. Chem. Soc. Pak. 5, 243–246 (1983) again showed that the nitrile oxide intermediate is formed by carrying the reaction out in the presence of an acetylenic compound as the dipolarophile to produce an isoxazole. Commercial utilization of this route has not been deemed suitable due to problems which include that the yield of the desired product is low, the acetic anhydride is consumed in the reaction, the conventional anhydride deemed useful yields by-products which are difficult to separate from the product mixture and the anhydride is an expensive material especially in view of the fact that it is consumed on a mole to mole basis with respect to the nitroalkane used.

It is desired to provide a process which can readily produce isoxazolines and isoxazoles in a manner which overcomes the defects discussed above. In particular, it is desired to provide a process which can form the desired product in high yields, which reduces by-product formation and provides an effective and efficient dehydrating agent.

SUMMARY OF THE INVENTION

The present invention is directed to a method of forming isoxazolines and isoxazoles by contacting, in the presence of a base, a primary nitroparaffin or certain nitroaromatic compounds with an organic cyclic dicarboxylic acid anhydride in the presence of a dipolarophile. The isoxazoline or isoxazole product is readily separated from the reaction media and the resultant dicarboxylic acid salt can be easily regenerated to the anhydride to be again reused as the dehydrating agent of additional nitrocompound. The cyclic anhydride can thus be used in small quantities to provide a commercially feasible and economically attractive process.

DETAILED DESCRIPTION

The present process is an improved method of forming isoxazolines and isoxazoles (depending on the dipolarophile used) from primary nitroparaffins. The process requires the use of a cyclic anhydride to unexpectedly provide a means of efficiently and effectively forming the desired product, separating the product and the resultant dicarboxylic acid or its salt and regenerating and recycling the spent anhydride to provide fresh dehydrating agent. The presently required anhydride provides a process where the cyclic anhydride can be used in very small molar quantities (substantially catalytic amounts) in comparison to the nitro compound used.

The reaction mechanism, although not meant to be a limitation on the subject invention, is believed to be as follows: a nitro compound contacts with anhydride and a base to form a nitrile oxide intermediate and a dicarboxylic acid/tertiary amine salt. The formed intermediate reacts with an olefinic or acetylenic dipolarophile to form an isoxazoline or isoxazole, respectively, while the dicarboxylic acid salt reforms to the anhydride upon application of heat and removal of water from the product medium.

The nitroalkanes or nitroparaffins which can be used can be represented by the formula, $RCH_2NO_2$ wherein R represents an aliphatic or aromatic group. Representative aliphatic groups include $C_1$–$C_{20}$ aliphatic hydrocarbons including methyl, ethyl, propyl, decyl and the like which, in addition, may be substituted with a group which is inert to the present process. Such groups include halogens, carboxylic acid esters, ethers and the like. The R group can also represent an aromatic group such as phenyl, and substituted phenyl groups in which the substitution group is inert to the reaction and the reactants. Such groups include alkyl, such as methyl, ethyl and the like; halogen such as chloro, bromo and the like; carboxylic acid esters such as methyl or ethyl esters of carboxylic acids, nitro group directly bonded to ring as well as other groups known to be substantially inert to the reactants and the conditions of the present process.

The dipolarophiles used in the present process can either be an olefinic or acetylenic compound. Olefinic compounds which are useful as the dipolarophile can be represented by the formula XCH=CHY wherein each X and Y is a group which is inert with respect to the subject reaction and, for example, can be independently selected from hydrogen, an alkyl such as methyl, ethyl, propyl, amyl and the like with $C_1$–$C_5$ being preferred; carboxylic acid ester; carboxylic acids; halogens such as chloro, bromo and the like; ethers, such as methoxy, ethoxy, phenoxy and the like; tertiary amino groups such as dimethylamino, diethylamino and the like; phenyl and substituted phenyl groups as well as a nitro group, a nitrile group, an acetate or the like. The alkyl and phenyl groups may be substituted with ester, halo or other groups which are substantially inert to the present reagents and conditions. It is preferred that at least one of the X and Y groups be hydrogen. The olefinic dipolarophile must be liquid or capable of being in a liquid state or at least partially dissolved in the liquid medium of the reaction when under the reaction conditions as described hereinbelow. Examples of olefinic dipolarophiles include propylene, 1-butene, 1-pentene, vinyl acetate, dimethyl maleate, diethyl maleate, diethyl fumarate, vinyl methyl ether and the like. The particular dipolarophile used will be determined by the particular product desired.

When the dipolarophile is selected from an olefinic compound as described above one attains an isoxazoline represented by the general formula:

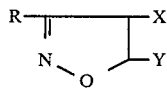

in which R, X and Y represent groups as described above.

The dipolarophile can be selected from an acetylenic compound having the general formula X—C≡C—Y in which X and Y are each independently selected from groups X and Y as defined above for the olefinic dipolarophiles. When the dipolarophile is an acetylenic compound the resultant product will be an isoxazole represented by the general formula:

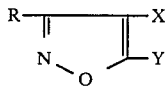

The present process requires the nitrocompound to be contacted with a cyclic dicarboxylic acid anhydride in the presence of the above described dipolarophile. The required anhydride can be represented by the general formula:

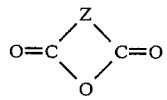

wherein Z represents a divalent organic hydrocarbon radical derived from an aliphatic or aromatic hydrocarbon in which two hydrogen atoms are removed from adjacent (1,2) or next to adjacent (1,3) carbon atoms. The aliphatic Z can be, for example, represented by

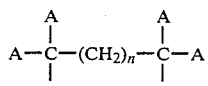

in which each A independently represent hydrogen or a lower alkyl group and n is an integer of 0 or 1. It is preferred that at least two of the A groups be hydrogen. The aromatic Z normally is bonded to each of the carbonyl groups by adjacent carbon atoms of the aromatic ring as, for example, phthalic anhydride. The aromatic ring may be substituted with other groups, such as alkyl groups to modify the physical properties of the anhydride and thus aid in separating it from the product solution, as more fully discussed below.

It has been unexpectedly found that by carrying out the subject synthesis with the use of a cyclic dicarboxylic acid anhydride, as described above, one unexpectedly achieves a process where the formed dicarboxylic acid or its salt may be readily separated, the product yield is improved, the by-product formation is lessened and the anhydride can be readily reformed and reused. In the most desired embodiment the presently required anhydrides are capable of being utilized in very small molar ratios in comparison to the nitro compound reactant. Although the molar ratio can be from about 20:1 to 1:20, it is preferred to utilize this capacity and, thereby, use the anhydride to nitro compound in molar ratios of from about 1:20 to 1:5.

The reaction is carried out in a manner that all of the reactants are in the liquid phase. The reaction can be carried out in an excess of one of the reactants or with an inert solvent. The inert solvent can be any organic liquid in which all of the reactants are miscible under the reaction conditions, and which is inert to carboxylic acids, anhydrides, nitro compounds and olefins and which is capable of being liquid under the reaction conditions. Examples of suitable solvent materials include excess of the nitroaromatic or nitroparaffin which is used as reactant, excess olefin to that used as reactant, aliphatic or aromatic saturated hydrocarbons, such as pentane, hexane, octane, benzene, toluene and the like; tertiary amines, such as triethylamine, n-octyl dimethylamine and the like; amides such as dimethyl formamide, N-methyl pyrrolidone and the like; esters such as ethyl acetate and the like; ethers such as diethyl ether, glyme and the like.

The reaction must be carried out in the presence of a base. The preferred base material is selected from a tertiary amine such as trialkyl amines as, for example, trimethylamine, triethylamine and the like. When a tertiary amine is used as a solvent, no additional amine is required. Other bases may be used such as alkali metal hydroxides or carbonates but because they will form salts with the free acid formed in the reaction and, thus, require neutralization, they are not preferred.

The reaction is carried out under temperature and pressure conditions which will maintain all of the reactants in solution or in liquid phase where no solvent is added. The temperature may range from about 30° to 250° C. with from about 50° to 180° C. being preferred. The pressure may be ambient although elevated pressure may be required to maintain the reactants in liquid phase, as discussed above. Thus, pressures may range from 1 to 100 bars or greater.

The isoxazoline or isoxazole product is separated from the dicarboxylic acid or its salt. The specific mode will depend upon the physical properties of the specific product formed and of the cyclic anhydride used. In certain instances the product will precipitate out of the reaction liquid and can be readily separated by filtration, decantation and the like. The remaining reaction liquid is then heated to temperatures of from about 30° to 250° C. This heating can be carried out under subatmospheric conditions to aid in the removal of water and in the reformation of the anhydride. The anhydride is thus readily formed and capable of being recycled to be used in formation of additional nitrile oxide. In other instances the isoxazoline or isoxazole may be a low boiling liquid which can be removed from the product stream by low temperature distillation and the anhydride is again readily regenerated by heating with water removal. When the product is a high boiling liquid, the anhydride may be first removed from the product stream by heating sufficiently to regenerate the anhydride and removing it by distillation (or sublimation in the case of phthalic anhydride or the like) or other known means and then recovering the product from the product stream by conventional means. The removal of water and heating of the solution can be continuously done to regenerate the anhydride and provide a continuous process.

The anhydride is generally recoverable to a large degree and, thus, when the process is continuous, the amount of anhydride required can be small in comparison to the nitro compound as it is readily regenerated in situ. The anhydride reacts with the nitro compound to produce the nitrile oxide intermediate and forms a dicarboxylic acid/tertiary amine salt. The reaction liquid need only be heated under the reaction conditions with provision for water removal to regenerate, in situ, the anhydride.

The present process permits the reuse (or continuous use) of the product stream as the reaction medium. Once the isoxazoline or isoxazole product is removed, the resultant liquid will contain residual dipolarophile, the dicarboxylic acid and the base. Where the dipolarophile has a boiling point higher than that of water, one merely needs to remove the water to cause reformation of anhydride and free base. This can be done in situ and thus provides a very simple and efficient process. Even when the dipolarophile is a low boiling material (lower than water) the resultant product solution can be recycled with accommodation for first capturing the remaining dipolarophile, removal of the water and then returning the resulting anhydride product stream and, if desired, the dipolarophile to the reaction zone.

The ability to provide a means of producing the desired products in an economically effective manner and with substantially little generation of by-products has unexpectedly been achieved by using a cyclic dicarboxylic acid, anhydride, as the sole dehydrating agent for forming the nitrile oxide.

The following examples are given for illustrative purposes only and are not meant to be a limitation on the subject invention as defined by the claims appended hereto. All parts and percentages are by weight unless otherwise stated.

EXAMPLE 1

A sealed reactor was charged with 1 mole of phthalic anhydride, 5 moles of 1-nitropropane, 0.75 moles of trimethylamine, and 3 moles of propylene. The reaction mixture was heated and agitated at 75° C. and 200 psi for 5 hours. The mixture was then distilled under vacuum to remove the isoxazoline (76% yield, based on phthalic anhydride) and recover unreacted nitropropane, propylene, and some trimethylamine. The residue was heated to about 160° under vacuum to substantially recover most of the phthalic anhydride and trimethylamine initially used.

EXAMPLE 2

A sealed reactor was charged with 3.34 moles of phthalic anhydride, 1 mole of ethyl acetate, 1.3 moles of triethylamine, 1 mole of 1-nitropropane and 2.42 moles of propylene. The reaction mixture was heated and agitated at 75° C. and 180 psi for 3.5 hours. The resultant mixture was then stripped under vacuum to remove the isoxazoline (65% yield based on 1-nitropropane), as well as propylene, ethylacetate, and some triethylamine. The residue was heated under vacuum to about 160° C. to sublime the phthalic anhydride for reuse and to distill off $H_2O$ and triethylamine. The volatiles, containing 3-ethyl-5-methylisoxazoline were redistilled under vacuum to recover the various starting materials and obtain pure isoxazoline.

EXAMPLE 3

A reactor was charged with 20.0 parts phthalic anhydride, 20.9 parts nitroethane, 34.0 parts 1-hexene and heated to reflux. Then, 13.8 parts of triethylamine was slowly added over a one hour period. The mixture was refluxed for 20 hours. The product mixture was vacuum fractionally distilled to provide 3-methyl-5-butylisoxazoline in good yields.

EXAMPLE 4

A reactor was equipped with a thermometer, magnetic stirrer, and a Dean-Stark apparatus. The receiver of the Dean-Stark apparatus was charged with dry molecular sieves capable of removing the water from the refluxing solvent (N,N-dimethylacetamide) prior to return to the reactor. The reactor was charged with 1 part phthalic anhydride, 2.1 parts octyl dimethylamine and 11.1 parts 1-decene and then heated to reflux. 1-nitropropane (6.25 parts) were added slowly over a 30 minute period. The system was refluxed for 24 hours with removal of water by the molecular sieve. The reaction mixture was then cooled and analyzed by $^1H$ NMR which showed the presence of 3-ethyl-5-octyl isoxazoline based on known spectrum for pure compound prepared by an alternative synthesis. The isoxazoline was confirmed by mass spectral data.

The NMR analysis further showed, from the ratio of the signals for the proton on the $C_5$ position of the isoxazoline ring to that of the protons on the aromatic ring (from charged phthalic anhyd.), that the reaction was catalytic with respect to the phthalic anhydride. At least 4 moles of the isoxazoline were formed per mole of anhydride charged.

EXAMPLE 5

A reactor was charged with 2.1 parts cis-1,2-cyclohexanedicarboxylic anhydride, 2.1 parts nitroethane and 7.0 parts 1-hexene and heated to reflux (67° C.). Then, 1.4 parts of triethyl amine was slowly added over a 10 minute period and the system was maintained at reflux for 16 hours. The main product was 3-methyl-5-butylisoxazoline which was determined by gas chromatography and confirmed by G.C./mass spectroscopy.

What is claimed:

1. A process for forming a product selected from an isoxazoline having the formula:

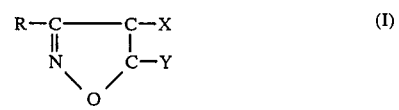

or an isoxazole of the formula:

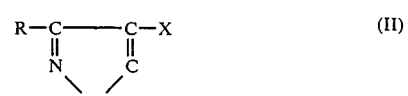

by contacting a liquid solution of (1) a primary nitrocompound represented by the formula $RCH_2NO_2$ in which R represents a $C_1$ to $C_{20}$ unsubstituted or substituted aliphatic hydrocarbon group or an unsubstituted or substituted phenyl group wherein said aliphatic substitution is selected from halogen, carboxylic acid esters and ethers and said phenyl substitution is selected from alkyl, halogen, carboxylic acid esters and nitro groups bonded directly on the ring, (2) a base selected from a tertiary amine, alkali metal hydroxide or alkali metal carbonate, (3) a cyclic orrganodicarboxylic acid anhydride, said acid anhydride represented by the formula

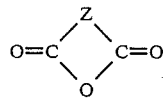

wherein Z is a divalent organic radical represented by

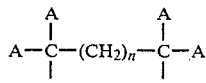

wherein each A independently represents hydrogen or lower alkyl or two of the A on different carbon atoms together represent a $C_4$-alkylene group and n is an integer of 0 or 1; or Z represents a benzene ring in which two hydrogen atoms are removed from adjacent carbons, and (4) a dipolarophile selected from an olefin represented by the formula $XCH=CHY$ to form compound I or an acetylene represented by the formula $XC\equiv CY$ to form compound II wherein each X and Y independently represents a group which is inert to the reactants and the subject reaction; separating the formed isoxazoline (I) or isoxazole (II), respectively; and heating the remaining solution to remove water and reform the cyclic acid anhydride.

2. The process of claim 1 wherein the reformed cyclic acid anhydride is utilized as component (3) with additional nitrocompound and dipolarophile.

3. The process of claim 1 wherein the molar ratio of anhydride to nitrocompound is from about 1:20 to about 1:5 and the base is tertiaryamine.

4. The process of claim 2 wherein the molar ratio of anhydride to nitrocompound is from about 1:20 to about 1:5 and the base is tertiaryamine.

5. The process of claim 3 wherein water removal and the product compound recovery is conducted substantially simultaneously to provide a continuous cyclic process.

6. The process of claim 4 wherein water removal and the product compound recovery is conducted substantially simultaneously to provide a continuous cyclic process.

7. The process of claim 1 wherein the dipolarophile is represented by the formula $XCH=CHY$ in which each X and Y independently represents hydrogen, $C_1$-$C_5$ alkyl, carboxylic acid, carboxylic acid esters, halogen, ether, tertiary-amino, nitro, nitrile, acetate or phenyl group and the product is an isoxazoline.

8. The process of claim 4 wherein the dipolarophile is represented by the formula $XCH=CHY$ in which each X and Y independently represents hydrogen, $C_1$-$C_5$ alkyl, carboxylic acid, carboxylic acid esters, halogen, ether, tertiary-amino, nitro, nitrile, acetate or phenyl group and the product is an isoxazoline.

9. The process of claim 6 wherein the dipolarophile is represented by the formula $XCH=CHY$ in which each X and Y independently represents hydrogen, $C_1$-$C_5$ alkyl, carboxylic acid, carboxylic acid esters, halogen, ether, tertiary-amino, nitro, nitrile, acetate or phenyl group and the product is an isoxazoline.

10. The process of claim 1 wherein the dipolarophile is represented by the formula $XC\equiv CY$ in which each X and Y independently represents hydrogen, $C_1$-$C_5$ alkyl, carboxylic acid, carboxylic acid ester, halogen, ether, tertiaryamino, nitro, nitrile, acetate or phenyl group and the product is an isoxazole.

11. The process of claim 4 wherein the dipolarophile is represented by the formula $XC\equiv CY$ in which each X and Y independently represents hydrogen, $C_1$-$C_5$ alkyl, carboxylic acid, carboxylic acid ester, halogen, ether, tertiaryamino, nitro, nitrile, acetate or phenyl group and the product is an isoxazole.

12. The process of claim 6 wherein the dipolarophile is represented by the formula $XC\equiv CY$ in which each X and Y independently represents hydrogen, $C_1$-$C_5$ alkyl, carboxylic acid, carboxylic acid ester, halogen, ether, tertiaryamino, nitro, nitrile, acetate or phenyl group and the product is an isoxazole.

13. The process of claim 7 wherein each Y and X independently represents hydrogen, a $C_1$-$C_5$ alkyl or a carboxylic acid ester group.

14. The process of claim 8 wherein each Y and X independently represents hydrogen, a $C_1$-$C_5$ alkyl or a carboxylic acid ester group.

15. The process of claim 9 wherein each Y and X independently represents hydrogen, a $C_1$-$C_5$ alkyl or a carboxylic acid ester group.

16. The process of claim 10 wherein each Y and X independently represents hydrogen, a $C_1$-$C_5$ alkyl or a carboxylic acid ester group.

17. The process of claim 11 wherein each Y and X independently represents hydrogen, a $C_1$-$C_5$ alkyl or a carboxylic acid ester group.

18. The process of claim 12 wherein each Y and X independently represents hydrogen, a $C_1$-$C_5$ alkyl or a carboxylic acid ester group.

19. The process of claim 7 wherein the cyclic acid anhydride is selected from phthalic anhydride or 1,2-cyclohexanedicarboxylic acid anhydride.

20. The process of claim 8 wherein the cyclic acid anhydride is selected from phthalic anhydride or 1,2-cyclohexanedicarboxylic acid anhydride.

21. The process of claim 9 wherein the cyclic acid anhydride is selected from phthalic anhydride or 1,2-cyclohexanedicarboxylic acid anhydride.

22. The process of claim 10 wherein the cyclic acid anhydride is selected from phthalic anhydride or 1,2-cyclohexanedicarboxylic acid anhydride.

23. The process of claim 11 wherein the cyclic acid anhydride is selected from phthalic anhydride or 1,2-cyclohexanedicarboxylic acid anhydride.

24. The process of claim 12 wherein the cyclic acid anhydride is selected from phthalic anhydride or 1,2-cyclohexanedicarboxylic acid anhydride.

25. The process of claim 1 characterized in that the reaction is carried out in an excess of one reactant or in an inert solvent selected from aliphatic hydrocarbon, aromatic hydrocarbon, tertiary amines, amides, esters or ethers.

26. The process according to claim 1 characterized in that the reaction is carried out at a temperature range of 30° to 250° C., and at pressures ranging from 1 to 100 bars.

* * * * *